(12) United States Patent
Haseloff et al.

(10) Patent No.: US 8,034,915 B2
(45) Date of Patent: Oct. 11, 2011

(54) GENE EXPRESSION CONSTRUCT

(75) Inventors: Jim Haseloff, Cambridgeshire (GB); Marlon Bauch, TP Houten (NL); Corinne Boisnard-Lorig, Lagry sur Narne (FR); Sarah Hodge, Cambridgeshire (GB); Laurent Laplaze, Montpellier (FR); John Runions, Oxford (GB); Smita Kurup, Harpenden (GB)

(73) Assignee: Cambridge University Technical Services Limited

( * ) Notice: Subject to any disclaimer, the term of this patent is extended or adjusted under 35 U.S.C. 154(b) by 254 days.

(21) Appl. No.: 10/490,285

(22) PCT Filed: Sep. 20, 2002

(86) PCT No.: PCT/GB02/04293
§ 371 (c)(1), (2), (4) Date: Sep. 12, 2004

(87) PCT Pub. No.: WO03/025172
PCT Pub. Date: Mar. 27, 2003

(65) Prior Publication Data
US 2005/0132432 A1 Jun. 16, 2005

(30) Foreign Application Priority Data

Sep. 21, 2001 (GB) .................................. 0122828.7

(51) Int. Cl.
*C07H 21/04* (2006.01)
*C12N 15/82* (2006.01)
(52) U.S. Cl. ....................................... 536/24.1; 800/278
(58) Field of Classification Search .................. None
See application file for complete search history.

(56) References Cited

U.S. PATENT DOCUMENTS

| | | | |
|---|---|---|---|
| 6,127,606 A | 10/2000 | Bennett et al. | |
| 6,147,282 A | 11/2000 | Goff et al. | |
| 6,362,394 B1 | 3/2002 | Crossland et al. | |
| 6,906,244 B2 * | 6/2005 | Fischer et al. | 800/298 |
| 7,022,513 B2 * | 4/2006 | Xu et al. | 435/255.1 |
| 2003/0165903 A1 * | 9/2003 | Dang et al. | 435/6 |

FOREIGN PATENT DOCUMENTS

| | | | |
|---|---|---|---|
| WO | 97/30164 A | | 8/1997 |
| WO | WO9730164 | * | 8/1997 |
| WO | WO 9730164 | * | 8/1997 |
| WO | 97/411228 | | 11/1997 |

OTHER PUBLICATIONS

Turcotte et al 1992 Gene & Devel. 6:2001-2009.*
Pfeifer et al. 1989, Cell 56:191-301.*
Pfeifer et al. 1989, Cell 56:191-301).*
Wu et al. (2003, The Plant Journal 35:418-427).*
Ha et al. 2000, Nucleic Acid Research 28:1026-1035.*
Todd et al; "Evolution of a Fungal Regulatory Gene Family: The Zn(II)2Cys6 Binuclear Cluster DNA Binding Motif"; Fungal Genetics and Biology, vol. 21, No. 3, 1997, pp. 388-405, XP002240288.
Pfeifer et al; "Functional Dissection and Sequence of Yeast HAP1 Activator"; Cell, vol. 56, No. 2, 1989, pp. 291-302, XP001148972.
Defranoux et al; "Functional Analysis of the Zinc Cluster Domain of the CYP1 (HAP1) Complex Regulator in Heme-Sufficient and Heme-Deficient Yeast Cells"; Molecular & General Genetics, vol. 242, No. 6, 1994, pp. 699-707, XP001148980.
Turcotte et al; "HAP1 Positive Control Mutants Specific for One of Two Binding Sites"; Genes & Development, vol. 6, No. 10, 1992, pp. 2001-2009.
Reichel et al; "Inefficient Expression of the DNA-Binding Domain of GAL4 in Transgenic Plants"; Plant Cell Reports, Springer Verlag, DE, vol. 14, 1995, pp. 773-776, XP000650425.
Sommer-Knudsen et al; "Hydroxyproline-Rich Plant Glycoproteins"; Phytochemistry, Pergamon Press, GB, vol. 47,No. 4, Feb. 1998, pp. 483-497, XP004293747.
Essl et al; "The N-Terminal 77 Amino Acids From Tobacco N-Acetylglucosaminyltransf Erase I Are Sufficient to Retain a Reporter Protein in the Golgi Apparatus of *Nicotiana benthamiana* Cells"; FEBS Letters, Elsevier Science Publishers, Amsterdam, NL, vol. 453, No. 1-2, Jun. 18, 1999, pp. 169-173, XP004259823.
Liu et al; "Green Fluorescent Protein As a Secretory Reporter and a Tool for Process Optimization in Transgenic Plant Cell Cultures"; Journal of Biotechnology, Elsevier Science Publishers, Amsterdam, NL, vol. 87, No. 1, Apr. 27, 2001, pp. 1-16, XP004231292.
Richardson et al; "Extracellular Secretion of *Aspergillus phytase* From *Arabidopsis* Enables Plants to Obtain Phosphorus From Phytate"; Plant Journal, vol. 25, No. 6, Mar. 2001, pp. 641-649, XP002247839.
NCBI Database—Search Results for "Zinc Finger Transcription Activator" [http://www.ncbi.nlm.nih.gov/entrez/query.fcgi?CMD=search&DB=protein]. Search performed on May 24, 2007.
Blau, et al., "Three Functional Classes of Transcriptional Activation Domains" *Molecular and Cellular Biology*, vol. 16, No. 5; pp. 2044-2055, (1996).
Ha et al., "Mutations in target DNA elements of yeast HAP1 modulate its transcriptional activity without affecting DNA binding," *Nucl. Acid Res.*, 1996, 24:8:1453-1459.
Hach et al., "The Coiled Coil Dimerization Element of the Yeast Transcriptional Activator Hap1, a Ga14 Family Member, Is Dispensable for DNA Binding but Differentially Affects Transcriptional Activation," *J. of Bio. Chem.*, 2000, 275:1:248-254.
Vuidepot et al., "NMR analysis of CYP1(HAP1) DNA binding domain-CYC1 upstream activation sequence interactions: recognition of a CGG trinucleotide and of an additional thymine 5 bp downstream by the zinc cluster and the N-terminal extremity of the protein," *Nucl. Acid. Res.*, 1997, 25:15:3042-3050.
Zhang et al., "The C6 zinc cluster dictates asymmetric binding by HAP1," *EMBO Journal*, 1996, 15:17:4676-4681.
Zhang et al., "The yeast activator HAP1-a GAL4 family member-binds DNA in a directly repeated orientation," *Genes & Dev.*, 1994, 8:2110-2119.

* cited by examiner

*Primary Examiner* — Li Zheng
(74) *Attorney, Agent, or Firm* — Fish & Richardson P.C.

(57) ABSTRACT

Provided are novel nucleic acid molecule encoding modified HAP1 DNA-binding domains. Also provided are novel reporter genes based on GFP and extension. The materials provided by the invention may be used in a variety of methods of activating genes having HAP1 upstream activation sequences in plants, which methods can be used to co-ordinate or investigate gene expression, optionally in conjunction with GAL4-regulated expression, and also in novel "enhancer" traps.

23 Claims, 8 Drawing Sheets

Figure 1 mHAP1-A

AAGCTTGGATCCAACAATGTCCTCCGACTCGTCCAAGATCAAGAGGAAGCGGAACCGCATCC
CGCTCAGCTGCACCATCTGCCGGAAGAGGAAGGTCAAGTGCGACAAGC mHAP1-B

TCAGGCCGCACTGCCAGCAGTGCACCAAGACCGGGGTGGCCCACCTCTGCCACTACATGGAG
CAGACCTGGGCCGAGGAGGCCGAGAAGGAGTTGCTGAAGGACAACGAGTT mHAP1-C

GAAGAAGCTCAGGGAGCGCGTGAAGTCCTTGGAGAAGACCCTCTCCAAGGTGCACTCCTCCC
CGTCGTCCAACTCCACGGCCCCCCCGACCGACGTCAGCCTGGGGGACGAGCTC mHAP1-D

GGCAGTGCGGCCTGAGCTTGTCGCACTTGA mHAP1-E

TCCCTGAGCTTCTTCAACTCGTTGTCCTTC mHAP1-5'

CGGCAAGCTTGGATCCAACAATG mHAP1-3'

CCCGGAGCTCGTCCCCCAGGCTG

Figure 2b

17/1                              47/11
atg tct tca gat tcg tcc aag atc aag agg aag cgt aac aga att ccg ctc agt tgc acc    HAP1
atg tcC tcC gaC tcg tcc aag atc aag agg aag cgG aac CgC atC ccg ctc agC tgc acc    mHAP1
 M   S   S   D   S   S   K   I   K   R   R   N   R   I   P   L   S   C   T 77/21                             107/31
att tgt cgg aaa agg aaa gtc aaa tgt gac aaa ctc aga cca cac tgc cag cag tgc act    HAP1
atC tgC cgg aaG agg aaG gtc aaG tgC gac aaG ctc agG ccG cac tgc cag cag tgc acC    mHAP1
 I   C   R   K   R   K   V   K   C   D   K   L   R   P   H   C   Q   Q   C   T 137/41                            167/51
aaa act ggg gta gcc cat ctc tgc cac tac atg gaa cag acc tgg gca gaa gag gca gag    HAP1
aaG acC ggg gtG gcc caC ctc tgc cac tac atg gaG cag acc tgg gcC gaG gag gcC gag    mHAP1
 K   T   G   V   A   H   L   C   H   Y   M   E   Q   T   W   A   E   E   A   E 197/61                            227/71
aaa gaa ttg ctg aag gac aac gaa tta aag aag ctt agg gag cgc gta aaa tct tta gaa    HAP1
aaG gaG ttg ctg aag gac aac gaG ttG aag aag ctC agg gag cgc gtG aaG tcC ttG gaG    mHAP1
 K   E   L   L   K   D   N   E   L   K   K   L   R   E   R   V   K   S   L   E 257/81                            287/91
aag act ctt tct aag gtg cac tct tct cct tcg tct aac tcc                            HAP1
aag acC ctC tcC aag gtg cac tcC tcC ccG tcg tcC aac tcc                            mHAP1
 K   T   L   S   K   V   H   S   S   P   S   S   N   S

Figure 2c

```
11/1                                      41/11
atg tcC tcC gaC tcg tcc aag atc aag agg aag cgG aac CGC atC ccg ctc agC tgc acc
 M   S   S   D   S   S   K   I   K   R   K   R   N   R   I   P   L   S   C   T 71/21                                     101/31
atC tgC cgg aaG agg aaG gtc aaG tgC gac aaG ctc agG ccG cac tgc cag cag tgc acC
 I   C   R   K   R   K   V   K   C   D   K   L   R   P   H   C   Q   Q   C   T 131/41                                    161/51
aaG acC ggg gtG gcc caC ctc tgc cac tac atg gaG cag acc tgg gcC gaG gag gcC gag
 K   T   G   V   A   H   L   C   H   Y   M   E   Q   T   W   A   E   E   A   E 191/61                                    221/71
aaG gaG ttg ctg aag gac aac gaG ttG aag aag ctC agg gag cgc gtG aaG tcC ttG gaG
 K   E   L   L   K   D   N   E   L   K   K   L   R   E   R   V   K   S   L   E 251/81                                    281/91
aag acC ctC tcC aag gtg cac tcC tcC ccG tcg tcC aac tcc ACG GCC CCC CCG ACC GAC
 K   T   L   S   K   V   H   S   S   P   S   S   N   S   T   A   P   P   T   D 311/101                                   341/111
GTC AGC CTG GGG GAC GAG CTC CAC TTA GAC GGC GAG GAC GTG GCG ATG GCG CAT GCC GAC
 V   S   L   G   D   E   L   H   L   D   G   E   D   V   A   M   A   H   A   D 371/121                                   401/131
GCG CTA GAC GAT TTC GAT CTG GAC ATG TTG GGG GAC GGG GAT TCC CCG GGG CCG GGA TTT
 A   L   D   D   F   D   L   D   M   L   G   D   G   D   S   P   G   P   G   F 431/141                                   461/151
ACC CCC CAC GAC TCC GCC CCC TAC GGC GCT CTG GAT ATG GCC GAC TTC GAG TTT GAG CAG
 T   P   H   D   S   A   P   Y   G   A   L   D   M   A   D   F   E   F   E   Q 491/161                                   521/171
ATG TTT ACC GAT GCC CTT GGA ATT GAC GAG TAC GGT GGG TAG
 M   F   T   D   A   L   G   I   D   E   Y   G   G   *
```

Figure 3b

GENE EXPRESSION CONSTRUCT

This application is the US national phase of international application PCT/GB02/04293, filed in English on 20 Sept. 2002, which designated the U.S. PCT/GB02/04293 claims priority to GB Application No. 0122828.7 filed 21 Sept. 2001. The entire contents of these applications are incorporated herein by reference.

TECHNICAL FIELD

The present invention relates generally to methods and materials for use in achieving and detecting gene expression, particularly localised expression of genes in a plant, and the detection of gene expression in a plant.

PRIOR ART

Developing multicellular tissues or organs generally demonstrate a capacity for self-organisation. For example, wounded tissues generally respond in a robust and coordinated fashion to allow repair, and local induction events can initiate prolonged and coordinated developmental processes. These types of developmental plasticity and functional autonomy are particularly evident in plant tissues. The basic features of a plant's body plan are established during embryogenesis, however its final form results from the continued growth of meristems and the formation of organs throughout its life, often in a modular and indeterminate fashion. Plant cells are constrained by rigid cell walls and are generally non-motile, so there is the clear possibility that cell fates within a meristem are determined by lineage. However, evidence from plant chimera and wounding studies have demonstrated a more important role for cell-cell interactions during fate determination (reviewed in Steeves & Sussex, Patterns in Plant Development, 1989) and laser ablation of cells within the *Arabidopsis* root meristem has shown that after the death of a cell, a neighbouring cell can be triggered to divide and compensate for the loss (van der Berg et al., *Nature* 378:62-65, 1995). It is likely that positional information during plant development is obtained via cell-cell contact, and that the coordination and fate of cells within a developing meristem may be determined by a network of local cellular interactions. The present inventors have chosen the *Arabidopsis* root meristem as a model system for investigating intercellular interactions. The root meristem possesses indeterminate growth and has a simple and transparent architecture. *Arabidopsis* is genetically amenable, and one can routinely generate transgenic lines for work with the intact organism.

However, in order to dissect and engineer local cell-cell interactions, it is crucial that one can (i) clearly visualise individual cells inside living meristems and (ii) have the means to perturb them. Over the past several years, the present inventors have developed a set of genetic and optical techniques which enable the manipulation and visualisation of cells within living plants.

In order to genetically manipulate cells during meristem development, the inventors have previously devised a scheme for targeted gene expression, which is based on a method widely used in *Drosophila* (Brand and Perrimon, Development 118:401-415, 1993). PCT/GB97/00406 describes a method using a highly modified transcription factor derived from the yeast GAL4 protein to form *Arabidopsis* plant lines that display localised expression of the foreign transcription factor, which can be used to trigger the ectopic expression of any other chosen gene at a particular time and place during the growth of the plant. The expression of the transcription factor can be followed using GFP as a reporter gene.

However, this system has a number of problems, one of which that it is limited in its application to the activation of a single chosen gene or the simultaneous activation of different genes within the same cell types, but does not allow the activation of different genes in different cell types and/or at different times within the same plant.

Thus it can be seen that another modified transcription factor which could be used in conjunction with or as an alternative to GAL4 would provide a valuable contribution to the art.

In order to visualise plant cells in transgenic plants, the gene encoding jellyfish green fluorescent protein (GFP) has been adapted for use as a reporter gene. The wild-type GFP cDNA is not expressed in *Arabidopsis*. The present inventors have extensively modified the gfp gene to remove a cryptic intron, to introduce mutations that confer improved folding and spectral properties and to alter the subcellular localisation of the protein. All of these alterations have been incorporated into a single modified form of the gene (mgfp5-ER) which can be routinely used for monitoring gene expression and marking cells in live transgenic plants (Siemering et al., Current Biology 6:1653-1663, 1996; Haseloff et al., PNAS 94:2122-2127, 1997).

Fluorescence microscopy techniques for high resolution observation of living cells have been developed. The expression of GFP within an organism produces an intrinsic fluorescence that colours normal cellular processes, and high resolution optical techniques can be used non-invasively to monitor the dynamic activities of these living cells. Using coverslip-based culture vessels, specialised microscope objectives and the optical sectioning properties of the confocal microscope, it is possible to monitor simply and precisely both the arrangement of living cells within a meristem, and their behaviour through long time-lapse observations. Further, the present inventors have recently constructed cyan and yellow emitting GFP variants that can be distinguished from the green fluorescent protein during confocal microscopy. These colour variants have enabled simultaneous imaging of different tagged proteins in living cells (Haseloff, J., "GFP variants for multispectral imaging of living cells", in Methods in Cell Biology, Vol. 58, Kay, S. and Sullivan, K. Eds. Academic Press (1999).

However, the usefulness of reporter proteins such as GFP is limited by the fact that, when plant tissues are cleared and stained for detailed 3-Dimensional analysis, reporter proteins such as GFP are lost from the tissues.

Thus it can be seen that a robust insoluble reporter protein would provide a valuable contribution to the art.

DISCLOSURE OF THE INVENTION

In a first aspect of the present invention there is provided an isolated nucleic acid, expressible in a plant cell, encoding at least an effective portion of a HAP1 DNA-binding domain, wherein the sequence has an A/T base content substantially reduced compared to the wild-type sequence.

"Effective Portion"

An effective portion of the DNA-binding domain is a portion sufficient to retain most (i.e. over 50%) of the DNA-binding activity of the full length DNA-binding domain. Preferably the "effective portion" comprises amino acid residues 1 to 94 of the yeast polypeptide, which we have found to be the minimal amount required to retain DNA binding activity. Typically, the "effective portion" will comprise at least 60% of the full-length sequence of the DNA-binding domain.

"A/T Base Content"

The A/T content of the wild-type yeast sequence encoding the DNA-binding domain of HAP1 is about 54%. The % A/T base content of the sequence of the invention encoding the effective portion of the HAP1 should be taken to be substantially reduced when it is less than 45%. Preferably, it will be less than 40%, most preferably it is 39%.

Preferably, the encoded polypeptide will have the identical amino acid sequence to the wild-type HAP1 polypeptide shown in FIG. 2b (bottom line). However, on the other hand, the encoded polypeptide may comprise an amino acid sequence which differs by one or more amino acid residues from the amino acid sequence shown in FIG. 2b (bottom line).

Nucleic acid encoding at least an effective portion of a HAP1 DNA-binding domain which is an amino acid sequence mutant, variant or derivative of the amino acid sequence shown in FIG. 2b, wherein the nucleic acid sequence has an A/T base content substantially reduced compared to the wild-type sequence is therefore included within the scope of the present invention.

A peptide which is an amino acid sequence variant, derivative or mutant of an amino acid sequence of a peptide may comprise an amino acid sequence which shares greater than about 60% sequence identity with the sequence of the amino acid sequence shown in FIG. 2b (bottom line), greater than about 70%, greater than about 80%, greater than about 90% or greater than about 95%. The sequence may share greater than about 70% similarity, greater than about 80% similarity, greater than about 90% similarity or greater than about 95% similarity with the amino acid sequence shown in FIG. 2b (bottom line).

For amino acid "homology", this may be understood to be similarity (according to the established principles of amino acid similarity, e.g. as determined using the algorithm GAP (as described below) or identity.

Amino acid similarity is generally defined with reference to the algorithm GAP (Genetics Computer Group, Madison, Wis.). GAP uses the Needleman and Wunsch algorithm to align two complete sequences that maximizes the number of matches and minimizes the number of gaps. Generally, the default parameters are used, with a gap creation penalty=12 and gap extension penalty=4. Use of GAP may be preferred but other algorithms may be used, e.g. BLAST (which uses the method of Altschul et al. (1990) J. Mol. Biol. 215: 405-410), FASTA (which uses the method of Pearson and Lipman (1988) PNAS USA 85: 2444-2448), or the Smith-Waterman algorithm (Smith and Waterman (1981) J. Mol. Biol. 147: 195-197), generally employing default parameters.

Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine.

In a preferred embodiment, the nucleic acid of the invention comprises the nucleic acid sequence of modified HAP1 (labelled mHAP1—middle line of FIG. 2b), which sequence has a substantially reduced A/T content relative to the wild-type yeast sequence which is shown in the top line of FIG. 2b, labelled HAP1 (substantially reduced base content is defined above).

In a preferred embodiment, the nucleic acid encoding the portion of HAP1 binding domain is fused to a nucleic acid sequence, said sequence being structural (e.g. encoding functional polypeptides) and/or regulatory. Preferably, said sequence encodes a transcriptional activator. The transcriptional activator may be the activation domain of the HAP1 protein, in which case the sequence encoding the HAP1 transcriptional activator should be optimised for expression in plants, by, for example, reducing the A/T content thereof. Alternatively, the transcriptional activator may be any transcriptional activator known by the skilled person to be active in plants. In such cases, the sequence of the invention thus encodes a chimeric polypeptide. In a preferred embodiment, the transcriptional activator domain is that of the herpes simplex virus (HSV) VP-16 (Greaves and O'Hare, J. Virol 63 1641-1650, (1989)). Preferably, the sequence comprises the nucleic acid sequence of VP16 shown in FIG. 2c (from nucleotide 293 onwards, i.e., the part of the top line of sequence which is in upper case). Thus in a preferred embodiment of the invention, there is provided a chimeric polypeptide comprising the nucleic acid sequence of the mHAP1-VPI6 chimera shown in FIG. 2c (i.e., the entire nucleotide sequence of FIG. 2c (top line)).

Other suitable transcriptional activation domains include certain peptides encoded by the E. coli genomic DNA fragments (Ma and Ptashne, Cell 51 113-119 (1987)) or synthetic peptides designed to form amphiphilic α-helix. (Giniger and Ptashne Nature 330 670-672 (1987)). A common requirement for suitable transcriptional activation domains is the need for excess charge (Gill and Ptashne, Cell 51 113-119 (1987), Estruch et al Nucl. Acids Res. 22 3983-3989 (1994)). Using this criteria, the skilled person is able to select or synthesise sequences which encode transcriptional activation activity in plants.

In a further aspect of the present invention, there is provided a nucleic acid construct, comprising the nucleic acid defined above.

Preferred Vectors

In one aspect of the present invention, the nucleic acid construct is in the form of a recombinant and preferably replicable vector. "Vector" is defined to include, inter alia, any plasmid, cosmid, phage or Agrobacterium binary vector in double or single stranded linear or circular form which may or may not be self transmissible or mobilizable, and which can transform a prokaryotic or eukaryotic host either by integration into the cellular genome or exist extrachromosomally (e.g. autonomous replicating plasmid with an origin of replication).

Generally speaking, those skilled in the art are well able to construct vectors and design protocols for recombinant gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, Molecular Cloning: a Laboratory Manual: 2nd edition, Sambrook et al, 1989, Cold Spring Harbor Laboratory Press or Current Protocols in Molecular Biology, Second Edition, Ausubel et al. eds., John Wiley & Sons, 1992.

A vector including nucleic acid according to the present invention need not include a promoter or other regulatory sequence, particularly if the vector is to be used to introduce the nucleic acid into cells for recombination into the genome.

Preferably the nucleic acid in the vector is under the control of, and operably linked to, an appropriate promoter or other regulatory elements for transcription in a host cell such as a microbial, e.g. bacterial, or plant cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell.

By "promoter" is meant a sequence of nucleotides from which transcription may be initiated of DNA operably linked downstream (i.e. in the 3' direction on the sense strand of double-stranded DNA).

"Operably linked" means joined as part of the same nucleic acid molecule, suitably positioned and oriented for transcription to be initiated from the promoter. DNA operably linked to a promoter is "under transcriptional initiation regulation" of the promoter.

Thus this aspect of the invention provides a gene construct, preferably a replicable vector, comprising a promoter operably linked to a nucleic acid provided by the present invention, for example, the sequence encoding the HAP1 DNA-binding domain.

Particularly of interest in the present context are nucleic acid constructs which operate as plant vectors. Specific procedures and vectors previously used with wide success upon plants are described by Guerineau and Mullineaux (1993) (Plant transformation and expression vectors. In: Plant Molecular Biology Labfax (Croy R R D ed) Oxford, BIOS Scientific Publishers, pp 121-148). Suitable vectors may include plant viral-derived vectors (see e.g. EP-A-194809).

Preferred Promoters

Preferably the promoter to be used in the construct is an "enhancer dependent" (or naïve) promoter, which requires the presence of a suitable enhancer sequence and appropriate transcription factors to cause substantial levels of transcription. Such naïve promoters correspond to the TATA box region of known plant promoters. "Plant promoters" should be understood to refer to promoters (e.g. viral or bacterial) active in a plant cell. The naïve promoter is in competent relationship with the sequence encoding the HAP1 DNA binding domain and transcription activation domain such that if the promoter is inserted into a plant host cell genome in functional relationship with an enhancer sequence and required transcription factors, the promoter will direct expression of the HAP1 DNA-binding domain in a tissue specific manner.

Reporter Genes

In preferred embodiments of the invention, a reporter gene operably linked to a HAP1 upstream activation sequence (UAS) is provided, such that the reporter gene will be expressed in response to synthesis of the transcriptional activator discussed above. The reporter gene may be present as part of a nucleic acid construct comprising the nucleic acid encoding an effective portion of a HAP1 DNA-binding domain. Alternatively, the reporter gene may be present in another nucleic acid construct.

The reporter gene may be any suitable reporter gene known to the skilled person as being active in plants. Use of a reporter gene facilitates determination of the UAS activity by reference to protein production. The reporter gene preferably encodes an enzyme which catalyses a reaction which produces a detectable signal, preferably a visually detectable signal, such as a coloured product. Many examples are known, including β-galactosidase and luciferase. β-galactosidase activity may be assayed by production of blue colour on substrate, the assay being by eye or by use of a spectrophotometer to measure absorbance. Fluorescence, for example that produced as a result of luciferase activity, may be quantitated using a spectrophotometer. Radioactive assays may be used, for instance using chloramphenicol acetyltransferase, which may also be used in non-radioactive assays. The presence and/or amount of gene product resulting from expression from the reporter gene may be determined using a molecule able to bind the product, such as an antibody or fragment thereof. The binding molecule may be labelled directly or indirectly using any standard technique.

Those skilled in the art are well aware of a multitude of possible reporter genes and assay techniques which may be used to determine UAS activity. Any suitable reporter/assay may be used and it should be appreciated that no particular choice is essential to or a limitation of the present invention.

In preferred embodiments of the invention, the reporter gene is GFP. The gfp gene may be the wild-type *Aequorea victoria* gene, or may be modified in any conventional way. For example, in a preferred embodiment, the gfp gene is mgfp5-ER, which has a cryptic intron removed, and has mutations which confer improved folding and spectral properties and altered subcellular localisation of the protein (Siemering et al., Current Biology 6:1653-1663, 1996; Haseloff et al., PNAS 94:2122-2127,1997).

However, although GFP (wild-type and modified forms) provides a convenient method of marking cells, clearing and staining of plant tissues normally result in loss of the green fluorescent protein from the tissues. For example, after treatment with even gentle clearing agents such as 50% ethanol or 50% glycerol, the protein becomes dislodged from treated cells.

The present inventors have overcome this problem by developing a new robust surface marker for visualisation of plant cells utilising GFP fused to an extensin protein (see below). Thus, in preferred embodiments of the invention, the reporter gene comprises the GFP extensin reporter gene fusion as described below.

Host Plants

In a further aspect of the invention, the invention provides a plant, plantlet or part thereof (e.g. a plant host cell or cell line) comprising a nucleic acid construct of the invention.

In preferred embodiments, the construct will have become stably integrated into a plant cell genome. In particular, the invention provides a plurality of plants, plantlets or parts thereof comprising a library, each plant or part thereof comprising a stably maintained nucleic acid sequence encoding an effective portion of the HAP1 DNA-binding domain as defined above. Preferably, the nucleic acid construct will be incorporated into the genome of plant cells present in the library. The library may be of any plant of interest to the skilled person. Suitable plants include maize, rice, tobacco, petunia, carrot, potato and *Arabidopsis*. Where the term "plant" is referred to hereinafter, unless context demands otherwise, it will be understood that the invention applies also to plantlets or parts of plants.

Each plant, plantlet or part thereof may have a particular pattern of expression of the integrated reporter gene. Thus, introduction of a further gene, having a HAP1-responsive UAS into the cells will result in the expression of the introduced gene in the same temporal/spatial pattern as the reporter gene, enabling expression of a gene of interest in selected tissues and/or at selected times.

Uses of Constructs of the Invention

In a preferred embodiment of the invention, the nucleic acid construct can be used in an "enhancer trap assay" to identify plant enhancer sequences (Sundaresan et al, Genes and Dev. 9 1797-1810). In such cases, the nucleic acid construct will preferably comprise right and left Ti-DNA, to enable random, stable insertion into the genome of a plant host cell.

As well as nucleic acid constructs for use in "enhancer trap assays", the invention further provides a method of identifying a plant "enhancer" nucleic acid sequence, comprising the steps of:

transforming a plant cell host with a nucleic acid construct comprising a naïve promoter sequence and a sequence encoding an effective portion of an HAP1 binding domain fused to a transcription activating domain, under the control of said naïve promoter sequence, wherein, when said plant is transformed with said construct such that the promoter is in functional relationship with a host cell enhancer sequence, the promoter will direct expression of said HAP1 binding domain operably linked to a transcription activating domain in the presence of "enhancer" transcription factors.

Thus the expression of said HAP1 binding domain operably linked to a transcription activating domain will indicate the presence of such an "enhancer" sequence. Optionally, the method includes the further step of identifying the position and nucleic acid sequence of the enhancer sequence.

For example, this may be performed by standard inverse PCR (I-PCR) or TAIL-PCR amplification of flanking sequences (see Sambrook & Russell, Molecular Cloning: a laboratory manual. $3^{rd}$ edition, CSHL press 2001: sections 4.75 (TAIL-PCR), 8-81 (I-PCR)).

The nucleic acid construct of the invention may thus also be used to control expression of an heterologous gene in a plant or part thereof. Thus in a further aspect of the present invention, there is provided a method of controlling expression of a gene of interest in a plant or part thereof comprising the steps of:

introducing the gene of interest into a plant or part thereof, said gene of interest having an HAP1 responsive upstream activation sequence, said plant or part thereof comprising a nucleic acid sequence encoding an effective portion of an HAP1 binding domain fused to a transcription activating domain, under the control of said naïve promoter such that expression of a transcriptional activator from said sequence is limited to those cell types in which a naïve promoter sequence is in functional relationship with a host cell enhancer sequence;

wherein binding of said transcriptional activator to said upstream activator sequence causes transcriptional activation of the gene of interest.

The nucleic acid of the invention enables the activation of different genes of interest in different cell types and/or at different times within the same plant, particularly wherein the nucleic acid encoding at least an effective portion of a HAP1 DNA-binding domain is used in conjunction with nucleic acid encoding a modified GAL4 transcription factor, for example that described in WO97/30164, the expression of each gene of interest being under the operable control of a different transcription factor.

Thus, included within the scope of the present invention is a method of independently controlling expression of a first and a second gene of interest in a plant comprising the steps of:

introducing the first gene of interest into a plant or part thereof, said first gene of interest having an HAP1 responsive upstream activation sequence;

introducing the second gene of interest into a plant or part thereof, said second gene of interest having a GAL4 responsive upstream activation sequence;

said plant or part thereof comprising a first nucleic acid sequence, which encodes a HAP1 transcriptional activator and a second nucleic acid sequence, which encodes a GAL4 transcriptional activator;

wherein binding of said HAP1 transcriptional activator to said upstream activator sequence causes transcriptional activation of the first gene of interest and binding of said GAL4 transcriptional activator to said upstream activator sequence causes transcriptional activation of the second gene of interest.

In this way, where the expression of the HAP1 transcriptional activator and the GAL4 transcriptional activator are each independently under the control of a different naïve promoter sequence, expression of each transcriptional activator is limited to those cell types in which the naïve promoter sequence is in functional relationship with a host cell enhancer sequence.

Moreover, using the nucleic acid construct of the invention, the simultaneous expression of a number of genes of interest may be controlled. Thus, in a further aspect of the invention, there is provided a method of co-ordinating the expression of a plurality of genes of interest in a plant or part thereof, comprising the steps of introducing the genes of interest into a plant or part thereof, said genes of interest each being under the control of an HAP1 responsive upstream activation sequence and said plant or part thereof comprising a nucleic acid sequence of the invention capable of expressing an HAP1 transcriptional activator, wherein binding of said HAP1 transcriptional activator to said upstream activator sequence causes transcriptional activation of the genes of interest.

The plurality of genes may all be associated with a single UAS, which facilitates their introduction into the plant or part thereof. Alternatively, one or more genes may be operably linked to a respective UAS.

Using the nucleic acid construct of the invention in conjunction with a nucleic acid construct encoding a GAL4 transcriptional activator, the expression of a first group of genes may be coordinated and the expression of a second group of genes may be co-ordinated, wherein each group of genes is expressed in different cell-types and/or at different times.

The gene or genes of interest may be any target gene or genes, the expression of which the researcher wishes to study. In preferred embodiments, the gene or genes of interest may be developmental genes or may encode one or more toxins. For example, a gene of interest may encode a toxin such as the A-chain of diphtheria toxin (DTA) and thus the method may be used to kill specific cells, for example, within the root meristem. Other genes of interest may encode one or more cell cycle regulatory proteins, in which case expression of such gene or genes may be used to drive misexpression of such proteins and activate or inhibit particular cell divisions e.g. within the root meristem. The gene or genes of interest may encode homeodomain proteins and thus the effect of their ectopic expression on cell fate determination may be studied.

The gene of interest may be of unknown function. Using the methods of the invention, the function of a gene of interest may be determined by comparing the phenotype of plants, or parts thereof in which the gene of interest is expressed with the phenotype of plants or parts thereof in which it is not expressed. Thus the invention extends to a method of determining the function of a gene of interest comprising the steps of:

introducing a gene of interest into a plant or part thereof, said gene of interest having an HAP1 responsive upstream activation sequence;

said plant or part thereof comprising a nucleic acid sequence, which encodes a HAP1 transcriptional activator;

wherein binding of said HAP1 transcriptional activator to said upstream activator sequence causes transcriptional activation of the gene of interest;

comparing the phenotype of said plant or part thereof in which said gene of interest is expressed with a second plant or part thereof in which said gene of interest is not expressed.

The gene or genes of interest may be "introduced" into the plant or part thereof using any conventional technique, for example, using any one of the vectors described above. Conveniently, the gene of interest is introduced using *Agrobacterium* mediated transformation.

In preferred embodiments of the methods of the invention, a reporter gene having an HAP1 responsive upstream activation sequence is provided, such that binding of said transcriptional activator to said upstream activator sequence causes transcriptional activation of the reporter gene. The reporter gene may be any suitable reporter gene, details of which are given above. Preferably, the reporter gene will be the extensin-GFP fusion gene described below.

Extensin-GFP Reporter Gene Construct

As described above, conventional cell markers utilising GFP suffer from the disadvantage that, during clearing of the tissues, the GFP is often lost to at least some degree. The present inventors have overcome this problem by developing a new robust surface marker for visualisation of plant cells utilising GFP.

This aspect of the invention is based on the inventors' demonstration that, when a coding sequence encoding GFP is fused to the coding sequence of the carrot extensin gene, the resulting expressed extensin-GFP fusion protein results in a bright marker resistant to clearing techniques which normally result in complete loss of GFP from treated tissues. Thus in a preferred embodiment of the present invention, the reporter gene construct is an extensin-GFP reporter gene.

Indeed the extensin-GFP reporter gene fusion forms a separate aspect of the present invention. Thus, this aspect of the present invention provides a gene fusion, expressible in a plant cell, comprising a nucleic acid sequence encoding a green fluorescent protein operably linked to a nucleic acid sequence encoding at least an effective portion of extensin.

An effective portion of extensin is a portion sufficient to retain most (i.e. over 50%) of the activity of the full length carrot extensin. Typically, the "effective portion" will comprise at least 60% of the full-length sequence of the carrot extensin. Wild-type extensin is involved in cell wall expansion in plants, other cell wall expansion proteins may be used, as would be understood by the person skilled in the art.

In a preferred embodiment, the nucleic acid sequence encoding the green fluorescent protein is the nucleic acid sequence of GFP shown in FIG. 3*b* (uppercase nucleic acid sequence) and/or the nucleic acid sequence encoding the extensin protein is the nucleic acid sequence of extensin shown in FIG. 3*b* (lowercase amino acid sequence). The gene fusion preferably comprises the a nucleic acid molecule having the entire sequence shown in FIG. 3*b*.

In one aspect of the present invention, the gene fusion is in the form of a recombinant and preferably replicable vector. Details of suitable vectors are those described above for the nucleic acid construct of the invention.

The extensin-GFP gene fusion is preferably part of a construct in which it is in operable relationship with an upstream activation sequence or promoter, the activation of which by an activation domain of a transcription factor causes expression of the extensin-GFP gene fusion.

In a further aspect of the invention, the invention provides a plant, plantlet or part thereof (e.g. a plant host cell or cell line) comprising the extensin-GFP gene fusion of the invention. In preferred embodiments, the extensin-GFP gene fusion will have become stably integrated into a plant cell genome.

Uses of Extensin-GFP Gene Fusion and Fusion Protein

The extensin-GFP gene fusion may be used in any of the applications for which a reporter gene may be routinely used, including those described above for "Reporter Genes".

In particular, the extensin-GFP gene fusion may be used to visualise specific patterns of cell-wall-localised expression in assays and methods as described herein.

Thus, for example, the invention provides the use of the extensin-GFP gene fusion of the invention in an enhancer trap assay. In a preferred embodiment, the "enhancer trap" assay is the "enhancer trap" assay described above. In such an assay, the extensin-GFP gene fusion is in operable relationship with an upstream activation sequence or promoter, the activation of which by an activation domain of an HAP1 binding domain operably linked to a transcription activating domain causes expression of the extensin-GFP gene fusion and thus enables the visualisation of expression of the HAP1 transcription factor.

Further included within the scope of the invention is the use of the extensin-GFP gene fusion in a method of cell sorting including the step of screening plants, plantlets, parts or cells thereof for extensin-GFP expression and selecting those plants, plantlets, parts or cells thereof which express GFP-extensin-GFP.

The cells expressing the extensin-GFP protein may be isolated using methods known to the skilled person, e.g. using antibody based sorting methods. For example, to isolate cell-types expressing extensin-GFP protein in a plant, e.g. *Arabidopsis*, from those not expressing the extensin-GFP protein, tissues from the transgenic plant may be treated with one or more enzymes e.g. pectinase, to liberate cells, followed by incubation with anti-GFP antibody coated magnetic particles. The purity of the magnetically isolated cells may be checked by fluorescence microscopy.

The same technique could be useful for studying the protein components of specific cell types, for example using antibody assays or fluorescent 2D gel display techniques. If unfixed cells are used, biochemical activities may be assayed. In addition, it is envisaged that sequential selection for different epitopes may be used to isolate cellular subpopulations. For example, if a cell wall GFP marker provided an epitope for the selection of certain cell types, a second independent marker could be used to select an even more specific sub-population (e.g. using a marker for a natural cell wall component).

Screening for Reporter Gene Expression in Plants

Expression of a reporter gene may be monitored using any suitable technique known to the person skilled in the art. For example, for the screening of shoots and roots of transgenic plantlets in which the reporter protein is a fluorescent protein such as GFP or the extensin-GFP of the invention, expression can be screened directly using epifluorescence microscopy, to, for example, monitor expression in developing meristems.

For the monitoring of expression of fluorescent proteins, multispectral dynamic imaging may be used. Such confocal microscope based methods allow high resolution observation of living cells. The expression of GFP within an organism produces an intrinsic fluorescence that colours normal cellular processes, and high resolution optical techniques can be used non-invasively to monitor the dynamic activities of these living cells. Using coverslip-based culture vessels, specialised microscope objectives and the optical sectioning properties of the confocal microscope, it is possible to monitor simply and precisely both the arrangement of living cells within a meristem, and their behaviour through long timelapse observations (see plantsci.cam.ac.uk/Haseloff). Further, the use of cyan and yellow emitting GFP variants that can be distinguished from the green fluorescent protein during confocal microscopy enable simultaneous imaging of different tagged proteins in living cells.

As a further or alternative screen, a second screen may be used on adult transgenic plants, in which parts of the plants such as the flowers or siliques are dissected and the fluorescence of parts monitored. Such screens are particularly useful for identifying expression patterns in embryos and floral parts, in which GFP may not be expressed in plantlets.

The invention will now be further described with reference to the following non-limiting Figures and Examples. Other embodiments of the invention will occur to those skilled in the art in the light of these.

FIGURES

FIG. 1 shows oligonucleotides for construction of mHAP1 DNA binding domain (SEQ ID Nos:1-7, respectively).

FIG. 2b shows the nucleic acid sequence of wild-type HAP1 (top line—labelled HAP1) (SEQ ID NO:8); the nucleic acid sequence of modified HAP1 (middle line—labelled mHAP1) (SEQ ID NO:10); and the encoded amino acid sequence (bottom line) (SEQ ID NO:9).

FIG. 2c shows the nucleic acid sequence (top line) of the mHAP1 VP16 synthetic transcription activator chimeric gene (SEQ ID NO:11), in which the HAP1 sequence is the modified sequence (running from the 5' terminus to position 292); the VP19 nucleic acid sequence runs from position 293 onwards and is shown in upper case); and the amino acid sequence of the synthetic transcription activator chimeric protein is shown in the bottom line (SEQ ID NO:12).

Figure 3A:
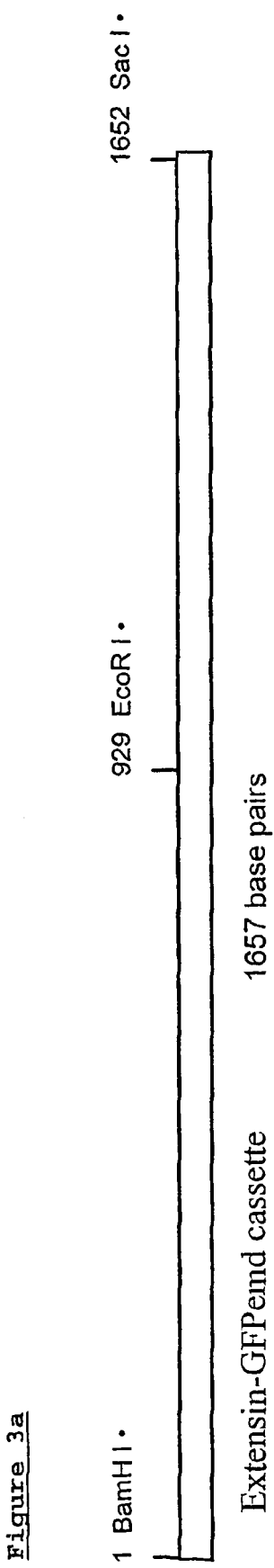

FIG. 3a shows a schematic diagram of the extensin-GFP gene fusion.

Figure 3B:
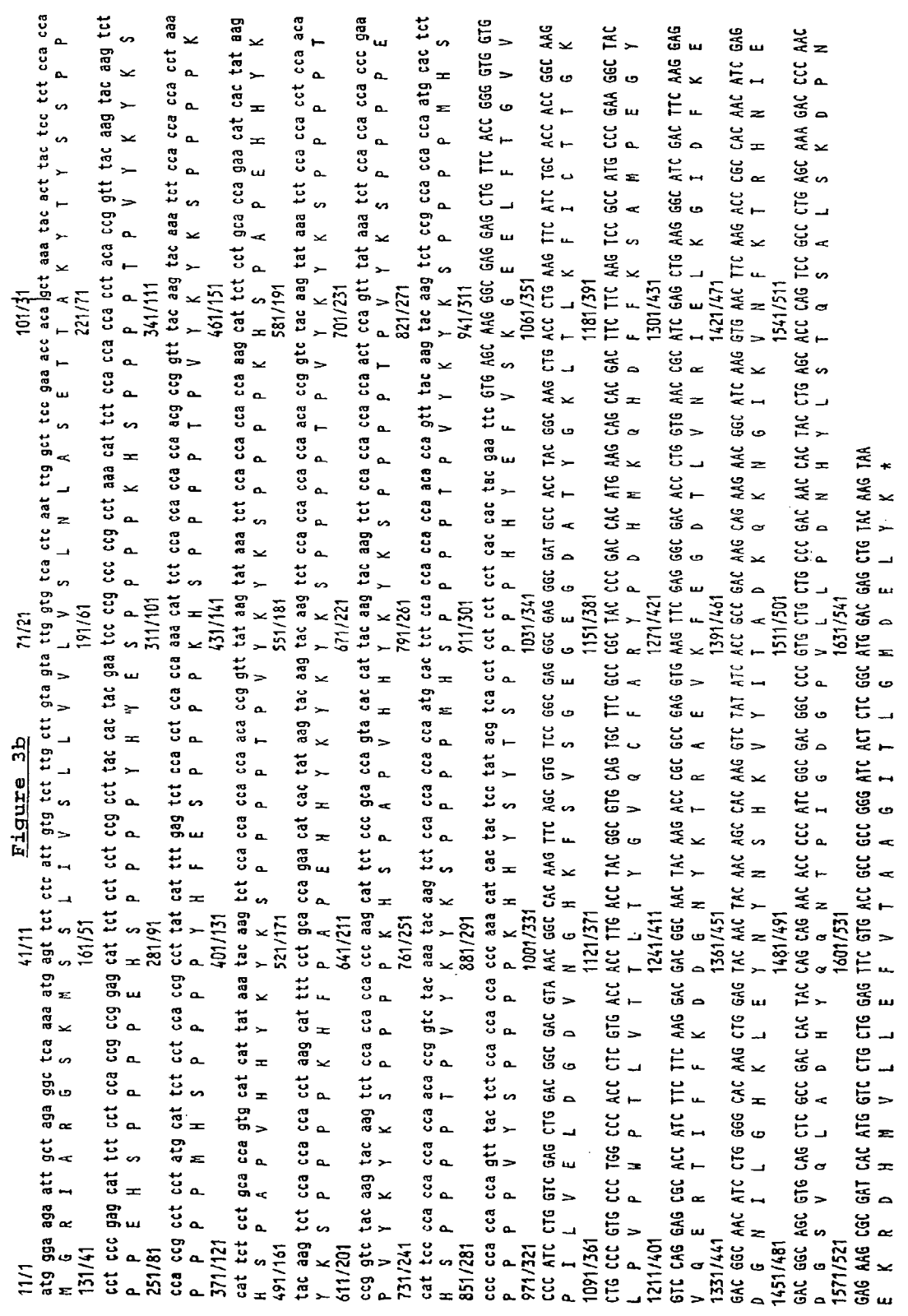

FIG. 3b shows the coding sequence of the extensin-GFP fusion of FIG. 3a in the top line (SEQ ID NO:13) and the encoded amino acid sequence in the bottom line (SEQ ID NO:14). Extensin nucleotide sequence is shown in lower case and the GFP nucleotide sequence is shown in uppercase.

Figure 4:

FIG. 4 shows expression of an extensin-GFP gene fusion in transgenic *Arabidopsis*. A 35S-extensin-GFP construction was introduced into *Arabidopsis* using *Agrobacterium* mediated transformation. Confocal optical sections of transformed plantlets are shown. Chlorophyll autofluorescence is seen in the red channel.

Figure 5:
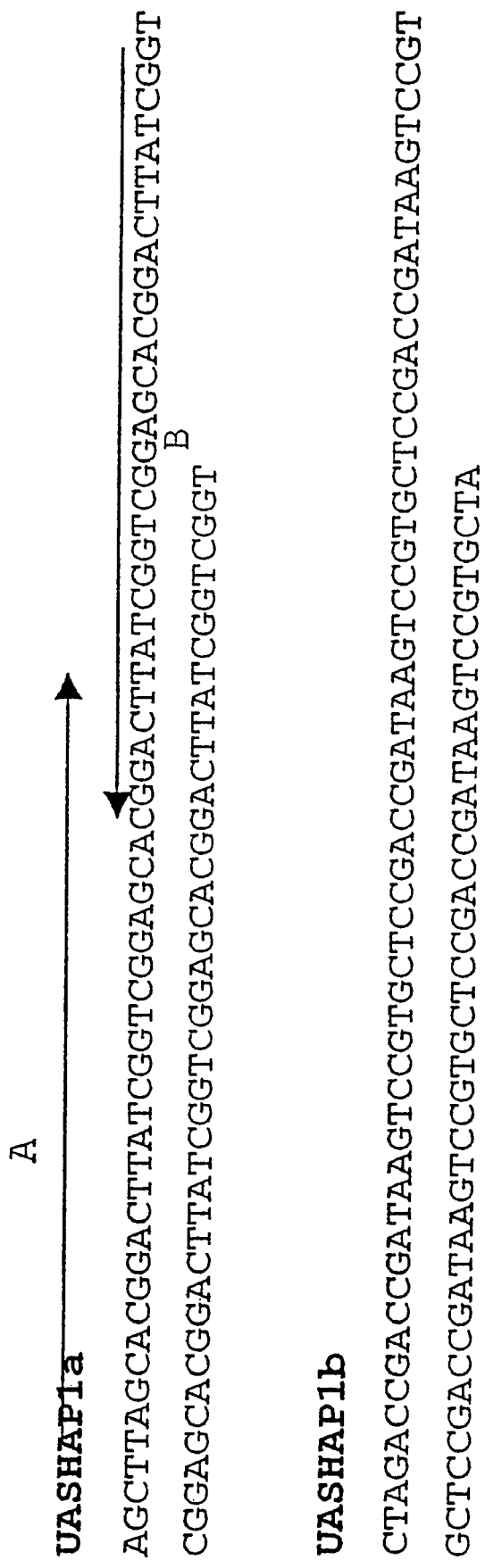

FIG. 5 shows oligonucleotides used in construction of a HAP1 DNA binding site (SEQ ID NO:15 and SEQ ID NO:16, respectively).

EXAMPLES

Example 1

Construction of the Modified HAP1-VP16 Gene

The yeast HAP1 protein is a member of a family of zinc-finger (Cys$_4$) transcription factors which are limited to fungi, and homologues have not been found in plants to date. Yeast genes have a high A/T content and are often poorly expressed in *Arabidopsis* due to aberrant post-transcriptional processing. A synthetic gene which has an elevated G/C content, and in which the DNA binding domain is fused to the highly active and G/C-rich transcription activator domain of VP16, was constructed:

Three long oligonucleotides, mHAP1-A, B & C (shown in FIG. 1) were made using automated synthesis on solid supports. The oligonucleotides encoded the predicted DNA binding domain of HAP1 protein with modified codon usage. Codon usage was modified according to the following criteria:

(i) GC content was increased
(ii) splice junction consensus sequences were avoided
(iii) the resultant amino acid sequence encoded by the nucleic acid was unchanged.

Oligonucleotides mHAP1-D and E (FIG. 1) contained complementary sequence corresponding to the junctions of the three longer oligonucleotides. The synthetic oligonucleotides were purified by polyacrylamide gel electrophoresis and phosphorylated after incubation with ATP and T4 polynucleotide kinase. The oligonucleotides were then mixed and heated at 94° C. for 1 min and annealed at 60° C. for 5 min. After cooling, the sample was treated with T4 DNA ligase to produce a small quantity of single-strand DNA corresponding to the mHAP1 DNA binding domain. This was then used as a template for PCR amplification with oligonucleotides mHAP1-5' and 3' (FIG. 1).

Figure 2A:
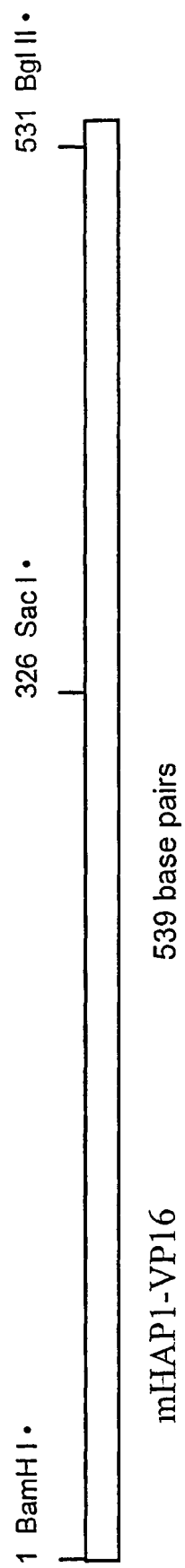
FIG. 2a shows a schematic diagram of the mHAP1-VP16 synthetic transcription activator chimeric gene

FIG. 2a shows in diagrammatic form the mHAP1-VP16 synthetic transcription activator chimeric gene (FIG. 2c entire sequence). The DNA sequence, encoding, in the 5' portion (bases 1 to 292), the modified HAP1 DNA binding domain (see also FIG. 2b middle sequence) and encoding, in the 3' portion (bases 293-533), the transcriptional activation domain from HSV VP16, is shown as the top sequence of FIG. 2c with the encoded amino acid sequence shown below. The SacI restriction endonuclease site within the gene is marked.

The wild-type sequence of the HAP1 binding domain (see the top sequence of FIG. 2b) is shown above for comparison of the A/T %. The wild-type HAP1 DNA binding domain DNA sequence is A/T rich.

Example 2

Construction of Insoluble GFP Marker

A variant of GFP was fused to the coding sequence of a carrot extensin. PCR amplification was used to obtain a copy of the extensin gene, isolated from carrots purchased in Cambridge market square. The carrot gene was genetically fused to a variant of green fluorescent protein obtained from Packard Biosciences (Meridian, Conn. (GFPemd).

A schematic diagram of the extensin-GFP gene fusion is shown in FIG. 3a with the coding sequence shown in FIG. 3b (top line), the encoded amino acid sequence is shown below in the bottom line of FIG. 3b. Extensin sequence is in lower case and GFP sequence is in uppercase.

Example 3

Expression of Extensin GFP Gene Fusion in Transgenic *Arabidopsis* a) Construction of the 35S-Extensin-GFP Construct.

A variant of GFP was fused to the coding sequence of a carrot extensin. PCR amplification was used to obtain a copy of the gene, isolated from carrots purchased in Cambridge market square. The carrot gene was genetically fused to a variant of green fluorescent protein obtained from Packard Bioscience (GFPemd (emerald)). Expression of this gene fusion in transgenic *Arabidopsis* tissues results in the decoration of cell walls with bright fluorescence.

Construction of the GFP-Extensin Gene

The following oligonucleotides were synthesised, and used as primers for the PCR amplification of the carrot extensin gene.

```
                                      (SEQ ID NO: 17)
CarExt5
GGC GGA TCC AAC AAT GGG AAG AAT TGC TAG AGG CTC (SEQ ID NO: 18)
CarExt3
GGC GGA TTC GTA GTG GTG AGG AGG AGG AGG TGA CGT
```

Substitute the Sequence Listing submitted herewith for the Sequence Listing filed Mar. 22, 2004.

Template carrot DNA was isolated using a Qiagen DNA extraction kit (UK—QIAGEN Ltd., Boundary Court, Gatwick Road, Crawley, West Sussex, RH10 9AX), and 1 microgram of isolated carrot DNA was used in a PCR reaction with VENT polymerase (New England Biolabs), (30 cycles: 92° C. 30 sec, 60° C. 30 sec, 72° C. 60 sec). The amplified product was purified by 1% agarose gel electrophoresis, and digested with the restriction endonucleases BamH1 and EcoR1. The cut fragment was then ligated into a plasmid vector that contained a GFP gene with an EcoR1 restriction fused to the N-terminus of the coding sequence, Haseloff, J., Siemering, K. R., Prasher, D. C. and Hodge, S Removal of a cryptic intron and subcellular localization of green fluorescent protein are required to mark transgenic *Arabidopsis* plants brightly. Proc. Natl. Acad. Sci. USA. 94, 2122-2127 (1997). The resulting plasmid contained a translational fusion between carrot extensin and the GFPemd gene (Packard Bioscience).

FIG. 3a shows a schematic diagram of the extensin-GFP gene fusion. The extensin sequences lie between the BamH1 and EcoR1 sites, and the GFP sequences lie between the EcoR1 and Sac1 sequences.

This reporter gene has been tested by insertion into plant transformation vectors, and expressed in transgenic *Arabidopsis* plants behind a constitutive CaMV 35S promoter, and as part of a HAP1-based enhancer trap vector. Bright, cell wall localised fluorescence results in both cases.

b) Transformation of *Arabidopsis thaliana*

*Arabidopsis thaliana* was transformed using the method given in PCT/GB97/00406.

Expression of the extensin-GFP gene fusion in transgenic *Arabidopsis* tissues results in the decoration of cell walls with bright fluorescence (FIG. 4). Extensin becomes covalently linked to the cell wall matrix, and the GFP-extensin marker is resistant to various clearing techniques that normally result in complete loss of the protein from treated tissues. For example, the cell wall bound signal is retained after glycerol infiltration.

Example 4

Construction of a HAP1 Promoter for Use in Plants

An optimised multimeric binding site for HAP 1 was synthesised and cloned behind a GFP promoter. Oligonucleotides used in the construction of the binding site are shown in FIG. 5 (UASHAP1a and UASHAP1b).

The oligonucleotides were phosphorylated using polynucleotide kinase, annealed, and ligated into the HinD III-Xba I sites of a $UAS_{GAL4}$ containing vector. The oligonucleotide sequences replaced the $UAS_{GAL4}$ with the appropriate $UAS_{HAP}1$ sequences—already positioned upstream of a plant TATA box and GFP reporter gene.

Example 5

Construction of HAP1-GFP Enhancer Trap Vector

An enhancer trap vector was constructed using the modified HAP1-VP16 gene positioned with a minimal (naïve) promoter and the extensin GFP gene fusion as described above.

The PCR product produced as described in Example 1 was cut with BamH1 and Sac1 restriction endonucleases and purified after electrophoresis through a 1.5% LGT agarose gel.

The plasmid pCMVGal65 (Cousens et al., EMBO J. 8:2337-2342, 1989) was used as a source of the VP16 sequence. A SacI-KpnI fragment, which encodes the activation domain of the herpes simplex virus VP16 protein, had been previously fused to a modified form of the GAL4 DNA binding domain (Haseloff and Hodge, U.S. Pat. No. 6,255, 558 B1) within a plant enhancer-trap vector, pET-15 (GAL4-GFP). The GAL4 sequence was excised from the pET-15 vector by restriction endonuclease digestion with BamH1 and Sac1, and replaced by ligation with the amplified mHAP1 sequence (see construction of extensin-GFP gene).

The mHAP1-VP16 gene was directly assayed for activity in transformed *Arabidopsis* plants by *Agrobacterium*-mediated transformation (Valvekens et al. Proc. Natl. Acad. Sci. USA 85:5536-5540, 1988).

Example 6

Enhancer Trap Screen

The vector was used to transform *Arabidopsis thaliana* using *Agrobacterium* mediated transformation as described in Example 3. In this way, large numbers of transgenic calli are regenerated, induced to form roots and shoots and are directly screened by epifluorescence microscopy for extensin-GFP expression in the developing meristems.

A suitable protocol is as follows:

(1) 20-100 transgenic *Arabidopsis* seed were placed in a 1.5 ml microfuge tube and washed for about 1 min with 1 ml of ethanol.

(2) Seeds were then incubated with 1 ml of a surface sterilising solution containing 1% (w/v) sodium hypochlorite and 0.1% (v/v) NP40 detergent, for 15 min at room temperature.

(3) The seeds were then washed three times with 1 ml of sterile water, and transferred by pipette to agar plates containing GM medium (Valvekens, D., Van Montagu, M and Van Lijsebettens, M. (1988) *Agrobacterium tumefaciens*-mediated transformation of *Arabidopsis thaliana* root explants by using kanamycin selection. *Proceedings of the National Academy of Sciences U.S.A.* 85:5536-5540).

---

1x Murashige and Skoog basal medium with Gamborgs B5 vitamins (Sigma)
1% sucrose
0.5 g/l 2-(N-morpholino)ethanesulfonic acid (MES)
0.8% agar
(adjusted to pH 5.7 with 1M KOH)
25 mg/l kanamycin was added if antibiotic selection of transgenic seedlings was necessary.

---

These procedures were performed in a laminar flow hood.

Alternatively, for extended timelapse imaging of roots, sterile seeds were sown in coverslip based vessels (Nunc) which comprised 4 wells, each containing about 400 µl of low gelling temperature agarose with GM medium. The roots of these plants grow down though the media and then along the surface of the coverslip. The roots are then ideally positioned for high resolution microscopic imaging through the base of the vessel.

(4) Sealed plates or vessels were incubated for 1-3 days in the dark at 4° C., and then transferred to an artificially lit growth room at 23° C. for germination.

(5) *Arabidopsis* seedlings germinate after 3 days, and can be used for microscopy for several weeks. Root and shoot tissues can be directly scored for GFP expression using an inverted fluorescence microscope (Leitz DM-IL) fitted with filter sets suitable for UV (Leitz-D; excitation filter 355-425 nm, dichroic mirror 455 nm, longpass emission filter 460 nm) and blue (Leitz-13; excitation filter 450-490 nm, dichroic mirror 510 nm, longpass emission filter 520 nm) light excitation of GFP. Roots, which grow along the base of the petri dish can be observed directly by epifluorescence microscopy through the clear plastic base. Shoot tissues were directly observed in inverted dishes by using one or two 7 mm threaded extension tubes with a 4× objective (EF 4/0.12), that gave greater working distances. Epifluorescence images were captured in Adobe Photoshop using a Sony DXC-930P 3-chip CCD video camera and F100-MPU integrating frame store, connected to a Nu Vista+ video digitiser in an Apple Macintosh computer.

GFP-expressing *Arabidopsis* seedlings were removed from agar media, and simply mounted in water under glass coverslips for microscopy. Growing roots could also be directly viewed through coverslip based vessels. Specimens were examined using a BioRad MRC-600 laser-scanning confocal microscope equipped with a 25 m W krypton-argon or argon ion laser and filter sets suitable for the detection of fluorescein and texas red dyes (BioRad filter blocks K1/K2 with krypton-argon ion laser, and A1/A2 with argon ion laser). We routinely use a Nikon 60× PlanApo N. A. 1.2 water immersion objective to minimise loss of signal through spherical aberration at long working distances. For the collection of timelapse images, the laser light source was attenuated by 99% using a neutral density filter, the confocal aperture was stopped down and single scans were collected at two second intervals. The large data files were transferred to an Apple Macintosh computer, and the programs PicMerge and 4DTurnaround were used with Adobe Photoshop and Premiere to produce QuickTime movies for display and analysis.

GFP fluorescence can be seen from 4 days after *Agrobacterium* inoculation, depending on the expression pattern. The plantlets exhibiting fluorescence can be used to construct a library of transformed plants.

Example 7

Transactivation mHAP1-VP16 expression within these lines can be used to direct the expression of a chosen gene at a precise time and place within the organism. The inventors have produced transgenic plants which maintain regulatory proteins or toxins, silent behind a HAP1-responsive promoter. These genes can now be activated in specific cells by crossing to a chosen mHAP1-VP16 expressing line.

A stable transformed line HJR1 of *Arabidopsis thaliana*, which forms part of the library described above, expresses modified GFP (under the influence of the mHAP1-VP16 activator) in the cells of the extreme root tip. Similar lines have also been produced which carry a localised cyan fluorescent protein, driven by the mHAP1-VP16 gene.

Using standard techniques, the line is crossed with another *Arabidopsis* line which comprises a silently maintained GUS reporter gene under operable control of a HAP1-responsive UAS. The plantlets obtained from the cross express GUS under the influence of the HAP1-VP16 transcriptional activator. The pattern of expression is the same as that for the GFP reporter gene in the parent cell line (i.e. at the extreme root tip). Thus the modified HAP1 DNA binding domain sequence is enables the expression of chosen genes of interest (e.g. GUS) in a predictable pattern and enables simultaneous expression of a plurality of genes of interest (e.g. GFP and GUS).

The invention claimed is:

1. An isolated nucleic acid molecule comprising a modified HAP1 DNA-binding domain nucleotide sequence fused to a transcriptional activator domain nucleotide sequence, said modified HAP1 DNA-binding domain nucleotide sequence encoding at least an effective portion of a HAP1 DNA-binding domain, said effective portion of said HAP1 DNA-binding domain determined by measuring binding in an electrophoretic mobility shift assay to a HAP1 upstream activation sequence, characterised in that said modified nucleotide sequence has an A/T base content of less than 45%, wherein said isolated nucleic acid molecule is capable of activating transcription of a second nucleotide sequence in a plant cell when said second nucleotide sequence is operably linked to a HAP1 upstream activation sequence.

2. A nucleic acid molecule as claimed in claim 1 wherein the effective portion comprises the amino acid sequence of SEQ ID NO:9.

3. A nucleic acid molecule as claimed in claim 1 wherein the modified nucleotide sequence has the nucleotide sequence of SEQ ID NO:10.

4. A nucleic acid molecule as claimed in claim 1 wherein the transcriptional activator domain is the HAP1 activation domain or the herpes simplex virus (HSV) VP-16 activation domain.

5. A nucleic acid molecule as claimed in claim 4 wherein the nucleic acid molecule encodes the amino acid sequence of the mHAP1-VP16 chimera as shown in SEQ ID NO:12.

6. A nucleic acid molecule as claimed in claim 5 wherein the modified nucleotide sequence and transcriptional activator domain nucleotide sequence consist of the sequence shown in SEQ ID NO:11.

7. A nucleic acid as claimed in claim 1, further comprising right and left Ti-DNA.

8. A nucleic acid as claimed in claim 1, wherein the nucleic acid is operably linked to a promoter for transcription in a plant cell, wherein the promoter is optionally an inducible promoter.

9. A nucleic acid as claimed in claim 8 wherein the promoter is a tissue specific promoter.

10. A nucleic acid as claimed in claim 1, further comprising a second nucleotide sequence operably linked to a HAP1 upstream activation sequence.

11. A nucleic acid as claimed in claim 10 wherein said second nucleotide sequence encodes a reporter polypeptide capable of generating a visually detectable signal.

12. A nucleic acid as claimed in claim 11 wherein the visually detectable signal can be monitored by multispectral dynamic imaging.

13. A nucleic acid as claimed in claim 11 wherein the reporter polypeptide is a wild-type or modified GFP.

14. A nucleic acid as claimed in claim 13 wherein the modified GFP is encoded by mgfp5-ER.

15. A composition of matter comprising: (i) a first nucleic acid molecule comprising a modified HAP1 DNA-binding domain nucleotide sequence fused to a transcriptional activator domain nucleotide sequence, said modified HAP1 DNA-binding domain nucleotide sequence encoding at least an effective portion of a HAP1 DNA-binding domain, said effective portion of said HAP1 DNA-binding domain determined by measuring binding in an electrophoretic mobility shift assay to a HAP1 upstream activation sequence, characterised in that said modified nucleotide sequence has an A/T base content of less than 45%, and (ii) a second nucleic acid molecule comprising a reporter nucleotide sequence consisting of a reporter gene operably linked to a HAP1 upstream activation sequence, wherein said first nucleic acid molecule is capable of activating transcription of said reporter gene when said first and second nucleic acid molecules are expressed in a plant cell.

16. A method of making a transgenic plant cell, which comprises introducing into a host plant cell, a nucleic acid molecule comprising a modified HAP1 DNA-binding domain nucleotide sequence fused to a transcriptional activator domain nucleotide sequence, said modified HAP1 DNA-binding domain nucleotide sequence encoding at least an effective portion of a HAP1 DNA-binding domain, said effective portion of said HAP1 DNA-binding domain determined by measuring binding in an electrophoretic mobility shift assay to a HAP1 upstream activation sequence, characterised in that said modified HAP1 DNA-binding domain nucleotide sequence has an A/T base content of less than 45%, wherein said nucleic acid molecule is capable of activating transcription of a second nucleotide sequence in a plant cell when said second nucleotide sequence is operably linked to a HAP1 upstream activation sequence.

17. A plant cell transformed with the nucleic acid of claim 1.

18. A method for producing a transgenic plant, which method comprises: (a) introducing into a plant cell a first nucleic acid molecule and a second nucleic acid molecule, said first nucleic acid molecule comprising a modified HAP1 DNA-binding domain nucleotide sequence fused to a transcriptional activator domain nucleotide sequence, said modified HAP1 DNA-binding domain nucleotide sequence encoding at least an effective portion of a HAP1 DNA-binding domain, said effective portion of a HAP1 DNA-binding domain determined by measuring binding in an electrophoretic mobility shift assay to a HAP1 upstream activation sequence, characterised in that said modified HAP1 DNA-binding domain nucleotide sequence has an A/T base content of less than 45%, and wherein said second nucleic acid molecule comprises a second nucleotide sequence operably linked to a HAP1 upstream activation sequence, and (b) growing a plant from the plant cell, wherein said plant is capable of expressing said second nucleotide sequence.

19. A transgenic plant made by the method of claim 18.

20. A plant as claimed in claim 19, further comprising a reporter nucleotide sequence consisting of a reporter gene operably linked to a HAP1 upstream activation sequence.

21. A method of making a transgenic plant cell which comprises introducing said first and second nucleic acids of claim 15 into a host plant cell.

22. A plant cell transformed with the first and second nucleic acids of claim 15, wherein said plant cell expresses said reporter gene.

23. A method of producing a transgenic plant, which method comprises growing a plant from the plant cell of claim 22, wherein said plant expresses said reporter gene.

* * * * *

UNITED STATES PATENT AND TRADEMARK OFFICE
CERTIFICATE OF CORRECTION

| | | |
|---|---|---|
| PATENT NO. | : 8,034,915 B2 | Page 1 of 1 |
| APPLICATION NO. | : 10/490285 | |
| DATED | : October 11, 2011 | |
| INVENTOR(S) | : Haseloff et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 271 days.

Signed and Sealed this
Thirty-first Day of July, 2012

David J. Kappos
*Director of the United States Patent and Trademark Office*

UNITED STATES PATENT AND TRADEMARK OFFICE
CERTIFICATE OF CORRECTION

PATENT NO.        : 8,034,915 B2                                     Page 1 of 1
APPLICATION NO.   : 10/490285
DATED             : October 11, 2011
INVENTOR(S)       : Jim Haseloff It is certified that error appears in the above-identified patent and that said Letters Patent is hereby corrected as shown below:

On the Title Page:
Column 1 (§371(c)(1), (2), (4) Date), delete "Sep. 12. 2004" and insert --Sep. 24, 2004-- therefor.

Signed and Sealed this
Fourth Day of December, 2012

David J. Kappos
*Director of the United States Patent and Trademark Office*

SEQUENCE LISTING

```
<160> NUMBER OF SEQ ID NOS: 18

<210> SEQ ID NO 1
<211> LENGTH: 110
<212> TYPE: DNA
<213> ORGANISM: Artificial Sequence
<220> FEATURE:
<223> OTHER INFORMATION: Description of Artificial Sequence:
      Oligonucleotide for construction of mHAP1 binding
      domain.

<400> SEQUENCE: 1
aagcttggat ccaacaatgt cctccgactc gtccaagatc aagaggaagc ggaaccgcat      60
cccgctcagc tgcaccatct gccggaagag gaaggtcaag tgcgacaagc                110

<210> SEQ ID NO 2
<211> LENGTH: 112
<212> TYPE: DNA
<213> ORGANISM: Artificial Sequence
<220> FEATURE:
<223> OTHER INFORMATION: Description of Artificial Sequence:
      Oligonucleotide for construction of mHAP1 binding
      domain.
```

-continued

```
<400> SEQUENCE: 2
tcaggccgca ctgccagcag tgcaccaaga ccggggtggc ccacctctgc cactacatgg      60
agcagacctg ggccgaggag gccgagaagg agttgctgaa ggacaacgag tt             112

<210> SEQ ID NO 3
<211> LENGTH: 115
<212> TYPE: DNA
<213> ORGANISM: Artificial Sequence
<220> FEATURE:
<223> OTHER INFORMATION: Description of Artificial Sequence:
      Oligonucleotide for construction of mHAP1 binding
      domain.

<400> SEQUENCE: 3
gaagaagctc agggagcgcg tgaagtcctt ggagaagacc ctctccaagg tgcactcctc      60
cccgtcgtcc aactccacgg ccccccgac cgacgtcagc ctggggacg agctc           115

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide for construction of mHAP1 binding
      domain.

<400> SEQUENCE: 4
ggcagtgcgg cctgagcttg tcgcacttga                                       30

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide for construction of mHAP1 binding
      domain.

<400> SEQUENCE: 5
tccctgagct tcttcaactc gttgtccttc                                       30

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide for construction of mHAP1 binding
      domain.

<400> SEQUENCE: 6
cggcaagctt ggatccaaca atg                                              23

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide for construction of mHAP1 binding
      domain.

<400> SEQUENCE: 7
cccggagctc gtcccccagg ctg                                              23
```

<210> SEQ ID NO 8
<211> LENGTH: 282
<212> TYPE: DNA
<213> ORGANISM: Saccharomyces cerevisiae
<220> FEATURE:
<221> NAME/KEY: CDS
<222> LOCATION: (1)..(282)

<400> SEQUENCE: 8

```
atg tct tca gat tcg tcc aag atc aag agg aag cgt aac aga att ccg    48
Met Ser Ser Asp Ser Ser Lys Ile Lys Arg Lys Arg Asn Arg Ile Pro
 1               5                  10                  15 ctc agt tgc acc att tgt cgg aaa agg aaa gtc aaa tgt gac aaa ctc    96
Leu Ser Cys Thr Ile Cys Arg Lys Arg Lys Val Lys Cys Asp Lys Leu
             20                  25                  30 aga cca cac tgc cag cag tgc act aaa act ggg gta gcc cat ctc tgc   144
Arg Pro His Cys Gln Gln Cys Thr Lys Thr Gly Val Ala His Leu Cys
         35                  40                  45 cac tac atg gaa cag acc tgg gca gaa gag gca gag aaa gaa ttg ctg   192
His Tyr Met Glu Gln Thr Trp Ala Glu Glu Ala Glu Lys Glu Leu Leu
     50                  55                  60 aag gac aac gaa tta aag aag ctt agg gag cgc gta aaa tct tta gaa   240
Lys Asp Asn Glu Leu Lys Lys Leu Arg Glu Arg Val Lys Ser Leu Glu
 65                  70                  75                  80 aag act ctt tct aag gtg cac tct tct cct tcg tct aac tcc           282
Lys Thr Leu Ser Lys Val His Ser Ser Pro Ser Ser Asn Ser
                 85                  90
```

<210> SEQ ID NO 9
<211> LENGTH: 94
<212> TYPE: PRT
<213> ORGANISM: Saccharomyces cerevisiae

<400> SEQUENCE: 9

```
Met Ser Ser Asp Ser Ser Lys Ile Lys Arg Lys Arg Asn Arg Ile Pro
 1               5                  10                  15

Leu Ser Cys Thr Ile Cys Arg Lys Arg Lys Val Lys Cys Asp Lys Leu
             20                  25                  30

Arg Pro His Cys Gln Gln Cys Thr Lys Thr Gly Val Ala His Leu Cys
         35                  40                  45

His Tyr Met Glu Gln Thr Trp Ala Glu Glu Ala Glu Lys Glu Leu Leu
     50                  55                  60

Lys Asp Asn Glu Leu Lys Lys Leu Arg Glu Arg Val Lys Ser Leu Glu
 65                  70                  75                  80

Lys Thr Leu Ser Lys Val His Ser Ser Pro Ser Ser Asn Ser
                 85                  90
```

<210> SEQ ID NO 10
<211> LENGTH: 282
<212> TYPE: DNA
<213> ORGANISM: Artificial Sequence
<220> FEATURE:
<223> OTHER INFORMATION: Description of Artificial Sequence: Modified HAP1

<400> SEQUENCE: 10

```
atgtcctccg actcgtccaa gatcaagagg aagcggaacc gcatcccgct cagctgcacc     60
atctgccgga gaggaaggt caagtgcgac aagctcaggc cgcactgcca gcagtgcacc    120
aagaccgggg tggcccacct ctgccactac atggagcaga cctgggccga ggaggccgag   180
aaggagttgc tgaaggacaa cgagttgaag aagctcaggg agcgcgtgaa gtccttggag   240
aagaccctct ccaaggtgca ctcctccccg tcgtccaact cc                      282
```

-continued

```
<210> SEQ ID NO 11
<211> LENGTH: 522
<212> TYPE: DNA
<213> ORGANISM: Artificial Sequence
<220> FEATURE:
<223> OTHER INFORMATION: Description of Artificial Sequence: mHAP1 -
      VP16 synthetic transcription activator chimeric gene
<220> FEATURE:
<221> NAME/KEY: CDS
<222> LOCATION: (1)..(522)

<400> SEQUENCE: 11 atg tcc tcc gac tcg tcc aag atc aag agg aag cgg aac cgc atc ccg      48
Met Ser Ser Asp Ser Ser Lys Ile Lys Arg Lys Arg Asn Arg Ile Pro
 1               5                  10                  15 ctc agc tgc acc atc tgc cgg aag agg aag gtc aag tgc gac aag ctc      96
Leu Ser Cys Thr Ile Cys Arg Lys Arg Lys Val Lys Cys Asp Lys Leu
             20                  25                  30 agg ccg cac tgc cag cag tgc acc aag acc ggg gtg gcc cac ctc tgc     144
Arg Pro His Cys Gln Gln Cys Thr Lys Thr Gly Val Ala His Leu Cys
         35                  40                  45 cac tac atg gag cag acc tgg gcc gag gag gcc gag aag gag ttg ctg     192
His Tyr Met Glu Gln Thr Trp Ala Glu Glu Ala Glu Lys Glu Leu Leu
     50                  55                  60 aag gac aac gag ttg aag aag ctc agg gag cgc gtg aag tcc ttg gag     240
Lys Asp Asn Glu Leu Lys Lys Leu Arg Glu Arg Val Lys Ser Leu Glu
 65                  70                  75                  80 aag acc ctc tcc aag gtg cac tcc tcc ccg tcg tcc aac tcc acg gcc     288
Lys Thr Leu Ser Lys Val His Ser Ser Pro Ser Ser Asn Ser Thr Ala
                 85                  90                  95 ccc ccg acc gac gtc agc ctg ggg gac gag ctc cac tta gac ggc gag     336
Pro Pro Thr Asp Val Ser Leu Gly Asp Glu Leu His Leu Asp Gly Glu
            100                 105                 110 gac gtg gcg atg gcg cat gcc gac gcg cta gac gat ttc gat ctg gac     384
Asp Val Ala Met Ala His Ala Asp Ala Leu Asp Asp Phe Asp Leu Asp
        115                 120                 125 atg ttg ggg gac ggg gat tcc ccg ggg ccg gga ttt acc ccc cac gac     432
Met Leu Gly Asp Gly Asp Ser Pro Gly Pro Gly Phe Thr Pro His Asp
    130                 135                 140 tcc gcc ccc tac ggc gct ctg gat atg gcc gac ttc gag ttt gag cag     480
Ser Ala Pro Tyr Gly Ala Leu Asp Met Ala Asp Phe Glu Phe Glu Gln
145                 150                 155                 160 atg ttt acc gat gcc ctt gga att gac gag tac ggt ggg tag             522
Met Phe Thr Asp Ala Leu Gly Ile Asp Glu Tyr Gly Gly
                165                 170

<210> SEQ ID NO 12
<211> LENGTH: 173
<212> TYPE: PRT
<213> ORGANISM: Artificial Sequence
<220> FEATURE:
<223> OTHER INFORMATION: Description of Artificial Sequence: Amino acid
      sequence of the synthetic transcription activator chimeric
      protein

<400> SEQUENCE: 12

Met Ser Ser Asp Ser Ser Lys Ile Lys Arg Lys Arg Asn Arg Ile Pro
 1               5                  10                  15

Leu Ser Cys Thr Ile Cys Arg Lys Arg Lys Val Lys Cys Asp Lys Leu
             20                  25                  30

Arg Pro His Cys Gln Gln Cys Thr Lys Thr Gly Val Ala His Leu Cys
         35                  40                  45

His Tyr Met Glu Gln Thr Trp Ala Glu Glu Ala Glu Lys Glu Leu Leu
     50                  55                  60
```

-continued

```
Lys Asp Asn Glu Leu Lys Lys Leu Arg Glu Arg Val Lys Ser Leu Glu
 65                  70                  75                  80

Lys Thr Leu Ser Lys Val His Ser Ser Pro Ser Ser Asn Ser Thr Ala
                 85                  90                  95

Pro Pro Thr Asp Val Ser Leu Gly Asp Glu Leu His Leu Asp Gly Glu
            100                 105                 110

Asp Val Ala Met Ala His Ala Asp Ala Leu Asp Asp Phe Asp Leu Asp
        115                 120                 125

Met Leu Gly Asp Gly Asp Ser Pro Gly Pro Gly Phe Thr Pro His Asp
    130                 135                 140

Ser Ala Pro Tyr Gly Ala Leu Asp Met Ala Asp Phe Glu Phe Glu Gln
145                 150                 155                 160

Met Phe Thr Asp Ala Leu Gly Ile Asp Glu Tyr Gly Gly
                165                 170
```

<210> SEQ ID NO 13
<211> LENGTH: 1641
<212> TYPE: DNA
<213> ORGANISM: Artificial Sequence
<220> FEATURE:
<223> OTHER INFORMATION: Description of Artificial Sequence: Coding
      sequence of extensin-GFP fusion
<220> FEATURE:
<221> NAME/KEY: CDS
<222> LOCATION: (1)..(1641)

<400> SEQUENCE: 13

```
atg gga aga att gct aga ggc tca aaa atg agt tct ctc att gtg tct      48
Met Gly Arg Ile Ala Arg Gly Ser Lys Met Ser Ser Leu Ile Val Ser
 1               5                  10                  15 ttg ctt gta gta ttg gtg tca ctc aat ttg gct tcc gaa acc aca gct      96
Leu Leu Val Val Leu Val Ser Leu Asn Leu Ala Ser Glu Thr Thr Ala
                 20                  25                  30 aaa tac act tac tcc tct cca cca cct ccc gag cat tct cct cca ccg    144
Lys Tyr Thr Tyr Ser Ser Pro Pro Pro Pro Glu His Ser Pro Pro Pro
             35                  40                  45 ccg gag cat tct cct cct ccg cct tac cac tac gaa tcc ccg ccc ccg    192
Pro Glu His Ser Pro Pro Pro Pro Tyr His Tyr Glu Ser Pro Pro Pro
         50                  55                  60 cct aaa cat tct cca cca cca cct aca ccg gtt tac aag tac aag tct    240
Pro Lys His Ser Pro Pro Pro Pro Thr Pro Val Tyr Lys Tyr Lys Ser
 65                  70                  75                  80 cca ccg cct cct atg cat tct cct cca ccg cct tat cat ttt gag tct    288
Pro Pro Pro Pro Met His Ser Pro Pro Pro Pro Tyr His Phe Glu Ser
                 85                  90                  95 cca cct cca cca aaa cat tct cca cca cca acg ccg gtt tac aag        336
Pro Pro Pro Pro Lys His Ser Pro Pro Pro Pro Thr Pro Val Tyr Lys
            100                 105                 110 tac aaa tct cca cca cca cct aaa cat tct cct gca cca gtg cat cat    384
Tyr Lys Ser Pro Pro Pro Pro Lys His Ser Pro Ala Pro Val His His
        115                 120                 125 tat aaa tac aag tct cca cca cca cca aca ccg gtt tat aag tat aaa    432
Tyr Lys Tyr Lys Ser Pro Pro Pro Pro Thr Pro Val Tyr Lys Tyr Lys
    130                 135                 140 tct cca cca cca cca aag cat tct cct gca cca gaa cat cac tat aag    480
Ser Pro Pro Pro Pro Lys His Ser Pro Ala Pro Glu His His Tyr Lys
145                 150                 155                 160 tac aag tct cca cca cca cct aag cat ttt cct gca cca gaa cat cac    528
Tyr Lys Ser Pro Pro Pro Pro Lys His Phe Pro Ala Pro Glu His His
                165                 170                 175
```

-continued

| | | |
|---|---|---|
| tat aag tac aag tac aag tct cca cca cca cca aca ccg gtc tac aag<br>Tyr Lys Tyr Lys Tyr Lys Ser Pro Pro Pro Pro Thr Pro Val Tyr Lys<br>           180                    185                  190 | | 576 |
| tat aaa tct cca cca cct cca aca ccg gtc tac aag tac aag tct cca<br>Tyr Lys Ser Pro Pro Pro Pro Thr Pro Val Tyr Lys Tyr Lys Ser Pro<br>           195                    200                  205 | | 624 |
| cca cca ccc aag cat tct ccc gca cca gta cac cat tac aag tac aag<br>Pro Pro Pro Lys His Ser Pro Ala Pro Val His His Tyr Lys Tyr Lys<br>         210                    215                  220 | | 672 |
| tct cca cca cca cca act cca gtt tat aaa tct cca cca cca ccc gaa<br>Ser Pro Pro Pro Pro Thr Pro Val Tyr Lys Ser Pro Pro Pro Pro Glu<br>225                  230                  235                  240 | | 720 |
| cat tcc cca cca cca cca aca ccg gtc tac aaa tac aag tct cca cca<br>His Ser Pro Pro Pro Pro Thr Pro Val Tyr Lys Tyr Lys Ser Pro Pro<br>                  245                  250                  255 | | 768 |
| cca cca atg cac tct cca cca cca aca cca gtt tac aag tac aag<br>Pro Pro Met His Ser Pro Pro Pro Thr Pro Val Tyr Lys Tyr Lys<br>              260                  265                  270 | | 816 |
| tct ccg cca cca cca atg cac tct ccc cca cca gtt tac tct cca<br>Ser Pro Pro Pro Pro Met His Ser Pro Pro Pro Val Tyr Ser Pro<br>              275                  280                  285 | | 864 |
| cca cca ccc aaa cat cac tac tcc tat acg tca cct cct cct cct cac<br>Pro Pro Pro Lys His His Tyr Ser Tyr Thr Ser Pro Pro Pro Pro His<br>         290                    295                  300 | | 912 |
| cac tac gaa ttc gtg agc aag ggc gag gag ctg ttc acc ggg gtg gtg<br>His Tyr Glu Phe Val Ser Lys Gly Glu Glu Leu Phe Thr Gly Val Val<br>305                  310                  315                  320 | | 960 |
| ccc atc ctg gtc gag ctg gac ggc gac gta aac ggc cac aag ttc agc<br>Pro Ile Leu Val Glu Leu Asp Gly Asp Val Asn Gly His Lys Phe Ser<br>                  325                  330                  335 | | 1008 |
| gtg tcc ggc gag ggc gag ggc gat gcc acc tac ggc aag ctg acc ctg<br>Val Ser Gly Glu Gly Glu Gly Asp Ala Thr Tyr Gly Lys Leu Thr Leu<br>              340                  345                  350 | | 1056 |
| aag ttc atc tgc acc acc ggc aag ctg ccc gtg ccc tgg ccc acc ctc<br>Lys Phe Ile Cys Thr Thr Gly Lys Leu Pro Val Pro Trp Pro Thr Leu<br>            355                  360                  365 | | 1104 |
| gtg acc acc ttg acc tac ggc gtg cag tgc ttc gcc cgc tac ccc gac<br>Val Thr Thr Leu Thr Tyr Gly Val Gln Cys Phe Ala Arg Tyr Pro Asp<br>        370                    375                  380 | | 1152 |
| cac atg aag cag cac gac ttc ttc aag tcc gcc atg ccc gaa ggc tac<br>His Met Lys Gln His Asp Phe Phe Lys Ser Ala Met Pro Glu Gly Tyr<br>385                  390                  395                  400 | | 1200 |
| gtc cag gag cgc acc atc ttc ttc aag gac gac ggc aac tac aag acc<br>Val Gln Glu Arg Thr Ile Phe Phe Lys Asp Asp Gly Asn Tyr Lys Thr<br>                  405                  410                  415 | | 1248 |
| cgc gcc gag gtg aag ttc gag ggc gac acc ctg gtg aac cgc atc gag<br>Arg Ala Glu Val Lys Phe Glu Gly Asp Thr Leu Val Asn Arg Ile Glu<br>              420                  425                  430 | | 1296 |
| ctg aag ggc atc gac ttc aag gag gac ggc aac atc ctg ggg cac aag<br>Leu Lys Gly Ile Asp Phe Lys Glu Asp Gly Asn Ile Leu Gly His Lys<br>            435                  440                  445 | | 1344 |
| ctg gag tac aac tac aac agc cac aag gtc tat atc acc gcc gac aag<br>Leu Glu Tyr Asn Tyr Asn Ser His Lys Val Tyr Ile Thr Ala Asp Lys<br>450                  455                  460 | | 1392 |
| cag aag aac ggc atc aag gtg aac ttc aag acc cgc cac aac atc gag<br>Gln Lys Asn Gly Ile Lys Val Asn Phe Lys Thr Arg His Asn Ile Glu<br>465                  470                  475                  480 | | 1440 |
| gac ggc agc gtg cag ctc gcc gac cac tac cag cag aac acc ccc atc<br>Asp Gly Ser Val Gln Leu Ala Asp His Tyr Gln Gln Asn Thr Pro Ile<br>                  485                  490                  495 | | 1488 |

-continued

```
ggc gac ggc ccc gtg ctg ctg ccc gac aac cac tac ctg agc acc cag      1536
Gly Asp Gly Pro Val Leu Leu Pro Asp Asn His Tyr Leu Ser Thr Gln
            500                 505                 510 tcc gcc ctg agc aaa gac ccc aac gag aag cgc gat cac atg gtc ctg      1584
Ser Ala Leu Ser Lys Asp Pro Asn Glu Lys Arg Asp His Met Val Leu
        515                 520                 525 ctg gag ttc gtg acc gcc gcc ggg atc act ctc ggc atg gac gag ctg      1632
Leu Glu Phe Val Thr Ala Ala Gly Ile Thr Leu Gly Met Asp Glu Leu
    530                 535                 540 tac aag taa                                                          1641
Tyr Lys
545
```

<210> SEQ ID NO 14
<211> LENGTH: 546
<212> TYPE: PRT
<213> ORGANISM: Artificial Sequence
<220> FEATURE:
<223> OTHER INFORMATION: Description of Artificial Sequence: Encoded
      amino acid sequence of extensin-GFP fusion

<400> SEQUENCE: 14

```
Met Gly Arg Ile Ala Arg Gly Ser Lys Met Ser Ser Leu Ile Val Ser
1               5                   10                  15

Leu Leu Val Val Leu Val Ser Leu Asn Leu Ala Ser Glu Thr Thr Ala
            20                  25                  30

Lys Tyr Thr Tyr Ser Ser Pro Pro Pro Glu His Ser Pro Pro Pro Pro
        35                  40                  45

Pro Glu His Ser Pro Pro Pro Tyr His Tyr Glu Ser Pro Pro Pro Pro
    50                  55                  60

Pro Lys His Ser Pro Pro Pro Thr Pro Val Tyr Lys Tyr Lys Ser Pro
65                  70                  75                  80

Pro Pro Pro Met His Ser Pro Pro Pro Tyr His Phe Glu Ser Pro Pro
                85                  90                  95

Pro Pro Pro Lys His Ser Pro Pro Pro Thr Pro Val Tyr Lys Tyr Lys
            100                 105                 110

Tyr Lys Ser Pro Pro Pro Lys His Ser Pro Ala Pro Val His His Tyr
        115                 120                 125

Lys Tyr Lys Ser Pro Pro Pro Thr Pro Val Tyr Lys Tyr Lys Ser Pro
    130                 135                 140

Pro Pro Lys His Ser Pro Ala Pro Glu His His Tyr Lys Tyr Lys Ser
145                 150                 155                 160

Pro Pro Pro Lys His Phe Pro Ala Pro Glu His His Tyr Lys Tyr Lys
                165                 170                 175

Tyr Lys Ser Pro Pro Pro Thr Pro Val Tyr Lys Tyr Lys Ser Pro Pro
            180                 185                 190

Pro Thr Pro Val Tyr Lys Tyr Lys Ser Pro Pro Pro Pro Lys His Ser
        195                 200                 205

Pro Ala Pro Val His His Tyr Lys Tyr Lys Ser Pro Pro Pro Thr Pro
    210                 215                 220

Val Tyr Lys Ser Pro Pro Pro Glu His Ser Pro Pro Pro Thr Pro Val
225                 230                 235                 240

Tyr Lys Tyr Lys Ser Pro Pro Pro Pro Met His Ser Pro Pro Pro Thr
                245                 250                 255

Pro Val Tyr Lys Tyr Lys Ser Pro Pro Pro Pro Met His Ser Pro Pro
            260                 265                 270

Pro Val Tyr Ser Pro
        275     280                 285
```

```
Pro Pro Pro Lys His His Tyr Ser Tyr Thr Ser Pro Pro Pro His
290                 295                 300

His Tyr Glu Phe Val Ser Lys Gly Glu Glu Leu Phe Thr Gly Val Val
305                 310                 315                 320

Pro Ile Leu Val Glu Leu Asp Gly Asp Val Asn Gly His Lys Phe Ser
                325                 330                 335

Val Ser Gly Glu Gly Glu Gly Asp Ala Thr Tyr Gly Lys Leu Thr Leu
            340                 345                 350

Lys Phe Ile Cys Thr Thr Gly Lys Leu Pro Val Pro Trp Pro Thr Leu
            355                 360                 365

Val Thr Thr Leu Thr Tyr Gly Val Gln Cys Phe Ala Arg Tyr Pro Asp
370                 375                 380

His Met Lys Gln His Asp Phe Phe Lys Ser Ala Met Pro Glu Gly Tyr
385                 390                 395                 400

Val Gln Glu Arg Thr Ile Phe Phe Lys Asp Asp Gly Asn Tyr Lys Thr
                405                 410                 415

Arg Ala Glu Val Lys Phe Glu Gly Asp Thr Leu Val Asn Arg Ile Glu
            420                 425                 430

Leu Lys Gly Ile Asp Phe Lys Glu Asp Gly Asn Ile Leu Gly His Lys
            435                 440                 445

Leu Glu Tyr Asn Tyr Asn Ser His Lys Val Tyr Ile Thr Ala Asp Lys
450                 455                 460

Gln Lys Asn Gly Ile Lys Val Asn Phe Lys Thr Arg His Asn Ile Glu
465                 470                 475                 480

Asp Gly Ser Val Gln Leu Ala Asp His Tyr Gln Gln Asn Thr Pro Ile
                485                 490                 495

Gly Asp Gly Pro Val Leu Leu Pro Asp Asn His Tyr Leu Ser Thr Gln
            500                 505                 510

Ser Ala Leu Ser Lys Asp Pro Asn Glu Lys Arg Asp His Met Val Leu
            515                 520                 525

Leu Glu Phe Val Thr Ala Ala Gly Ile Thr Leu Gly Met Asp Glu Leu
530                 535                 540

Tyr Lys
545

<210> SEQ ID NO 15
<211> LENGTH: 106
<212> TYPE: DNA
<213> ORGANISM: Artificial Sequence
<220> FEATURE:
<223> OTHER INFORMATION: Description of Artificial Sequence:
      Oligonucleotide used in construction of a HAP1 DNA
      binding site

<400> SEQUENCE: 15
agcttagcac ggacttatcg gtcggagcac ggacttatcg gtcggagcac ggacttatcg    60
gtcggagcac ggacttatcg gtcggagcac ggacttatcg gtcggt               106

<210> SEQ ID NO 16
<211> LENGTH: 106
<212> TYPE: DNA
<213> ORGANISM: Artificial Sequence
<220> FEATURE:
<223> OTHER INFORMATION: Description of Artificial Sequence:
      Oligonucleotide used in construction of a HAP1 DNA
      binding site
```

```
-continued

<400> SEQUENCE: 16
ctagaccgac cgataagtcc gtgctccgac cgataagtcc gtgctccgac cgataagtcc        60
gtgctccgac cgataagtcc gtgctccgac cgataagtcc gtgcta                      106

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 17
ggcggatcca acaatgggaa gaattgctag aggctc                                  36

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 18
ggcggattcg tagtggtgag gaggaggagg tgacgt                                  36
```